United States Patent [19]

Thees et al.

[11] 4,429,700
[45] Feb. 7, 1984

[54] BLOOD PRESSURE MEASURING DEVICE

[75] Inventors: Richard Thees, Aachen; Rolf Wilden, Roetgen, both of Fed. Rep. of Germany

[73] Assignee: Honeywell B.V., Amsterdam, Netherlands

[21] Appl. No.: 230,829

[22] Filed: Feb. 2, 1981

[30] Foreign Application Priority Data

Feb. 4, 1980 [DE] Fed. Rep. of Germany ....... 3004011

[51] Int. Cl.³ .............................................. A61B 5/02
[52] U.S. Cl. .................... 128/681; 128/682; 128/686
[58] Field of Search ............... 128/677, 678, 680, 681, 128/682, 686

[56] References Cited

U.S. PATENT DOCUMENTS 3,224,435  12/1965  Traite ................... 128/682

FOREIGN PATENT DOCUMENTS 728835  4/1980  U.S.S.R. ...................... 128/677

Primary Examiner—Robert W. Michell
Assistant Examiner—John C. Hanley
Attorney, Agent, or Firm—Mitchell J. Halista; Trevor B. Joike

[57] ABSTRACT

An inflatable blood pressure cuff is pressurized with a vapor which is produced by heating a fluid which has a boiling point between 290° K. and 340° K. with an electric heating element. The heating element may comprise a PTC resistor which is disposed within the fluid. A piezoresistive element may also be disposed in the fluid to detect pressure pulses associated with Korotkoff sound.

8 Claims, 6 Drawing Figures

BLOOD PRESSURE MEASURING DEVICE

FIELD OF INVENTION

The invention relates to a blood pressure measuring device, comprising a cuff which can be applied to a part of a body, preferably a finger, and also comprising a measuring device for measuring the pressure in the cuff. For the measurement of the blood pressure, the cuff is inflated until the flow of blood through the artery is blocked. When the pressure in the cuff is gradually reduced, the pulse can be detected again in the artery at a given pressure (systolic blood pressure) or a "sound" (Korotkoff's sound) which is synchronized with the pulse occurs in the artery. When the pressure in the cuff is further reduced, the Korotkoff's sound suddenly becomes softer at a given pressure (diastolic blood pressure). The blood pressure measurement mainly concerns the determination of these two blood pressure values.

BACKGROUND OF INVENTION

In known devices of this kind, the cuff is generally applied to the upper arm of the patient. However, there are also blood pressure measuring devices where the cuff is slid onto a finger (for example, see DE-OS No. 18 17 089 and 28 42 337). Blood pressure measurements can thus be performed with high accuracy when it is ensured that the finger whereto the cuff is applied is situated approximately at the level of the heart during measurement, so that static pressure differences do not have an effect.

The inflation of the cuff is manually performed for some blood pressure measurements; this necessitates some experience in order to ensure that the pressure in the cuff will not be too high or too low. In other blood pressure measuring devices, it is merely necessary for the user to activate a pump which inflates the cuff. Such blood pressure measuring devices, however, are expensive.

SUMMARY OF THE INVENTION

The invention has for its object to provide a blood pressure measuring device which enables non-manual inflation of the cuff by means of simple means.

This object is achieved in accordance with the invention in that a part of the cuff or a reservoir which communicates with the cuff is filled with a liquid whose boiling point is between 290° K. and 340° K., a heating element which can be connected to a current or voltage source, being arranged in the liquid.

The cuff is inflated by connecting the heating element to the current or voltage source. The temperature of the liquid then rises and hence also its vapour pressure, until the atmospheric pressure is exceeded and the cuff is inflated.

Besides said temperature-dependency of the vapour pressure, the liquid should also exhibit an as low as possible thermal capacity and as little as possible evaporation heat in order to minimize the supply of energy for the inflation of the cuff. Suitable liquids are, for example, diethylether or acetone.

The heating element must always be immersed in the liquid. Therefore, if the liquid is not present in a separate reservoir, (preferably below the cuff) but in a part of the cuff, it must be ensured that the heating element is always present in the lowest parts of the cuff where the liquid collects.

The invention can in principle also be used for blood pressure measuring apparatus where the cuff is to be applied to the upper arm. In that case, however, the volume of the cuff is larger, which necessitates a larger liquid volume and hence a correspondingly higher heating power of the heating element.

In a preferred embodiment, the heating element is formed by a PTC resistor. On the basis of the positive temperature coefficient, it will almost be impossible to exceed a given temperature which is dependent on the value of the PTC resistor and the heating voltage if the impedance of the heating voltage source is sufficiently low: if the temperature were to increase, the resistance of the PTC resistor would increase, thus reducing the electric power generated therein; resulting in a decrease of the temperature. However, if the temperature were to decrease, the resistance would also decrease, and the power generated in the PTC resistor would increase so that the temperature would again increase.

In a further embodiment in accordance with the invention, the measuring device for measuring the pressure in the cuff comprises a temperature sensor as well as a memory in which the temperature/vapour pressure characteristic of the liquid is stored, and also a control device which determines the vapour pressure associated with the relevant temperature. Instead of the pressure measurement, a temperature measurement is then performed where the pressure associated with the temperature each time measured is determined from the temperature/vapour pressure characteristic.

In a further embodiment in accordance with the invention, this temperature measurement is particularly simple because the PTC resistor is used as the temperature sensor. The PTC resistor thus acts as the heating element prior to the measurement and as the measuring element during the measurement. The current flowing therethrough must be substantially smaller, of course, during the measurement.

In a further embodiment in accordance with the inventions a piezoresistive element is provided in the cuff or the reservoir for the pressure measurement. The resistance of this piezoresistive element changes as the pressure changes. The pressure variations caused by the Korotkoff's sounds become apparent as resistance variations in an element of this kind, and these resistance variations can be used for determining the systolic and the diastolic blood pressure.

BRIEF DESCRIPTION OF THE DRAWINGS

An embodiment in accordance with the invention will be described in detail hereinafter with reference to the accompanying diagrammatic drawing.

DETAILED DESCRIPTION OF THE INVENTION

Figure 1:
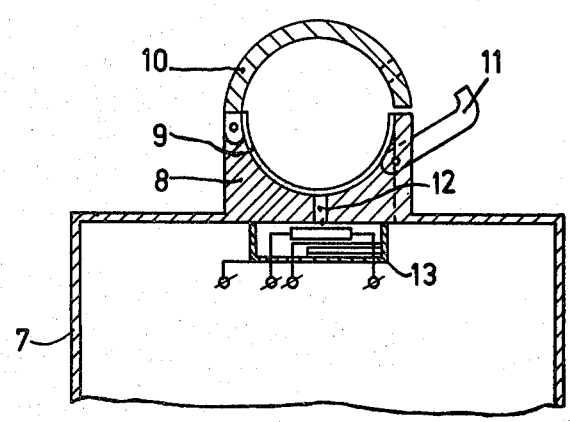
FIG. 1 is a sectional view of a housing of a blood pressure measuring device.
Figure 2:
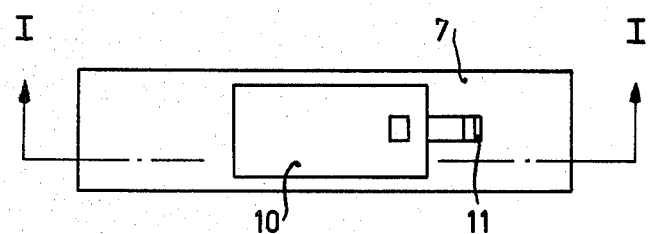
FIG. 2 is a plan view of such a device.

As is shown in the FIGS. 1 and 2, a semi-circular lower portion 8 in which a cuff 9 is inserted is mounted on a housing 7.

For the measurement, the patient places a finger on the cuff, after which the finger is fixed by means of a pivotable upper portion 10 which can be locked by means of an elastic hook 11. As is particularly clearly shown in FIG. 3, underneath the semicircular lower part there is provided a reservoir 13 which is filled with a liquid 14 and which communicates with the cuff 9 via a bore 12.

The liquid in the reservoir must have the following properties:

the vapour pressure does not exceed atmospheric pressure, at room temperature (293° K.), at a temperature which is not uncomfortable for humans during brief periods of time (from 300° K. to 340° K.), the vapour pressure is from approximately 200 mbar to 280 mbar above atmospheric pressure, the thermal capacity and the evaporation heat of the liquid are as low as possible.

Suitable liquids are, for example, diethylether and acetone. Diethylether has a vapour pressure of approximately 550 mbar at a temperature of 20° C. and a vapour pressure of approximately 1200 mbar at 40° C. Acetone has a vapour pressure of approximately 250 mbar at room temperature and a vapour pressure of approximately 1200 mbar at 60° C. Further suitable liquids are fluorinated hydrocarbons. Two of these liquids are $C Cl F_2-C Cl_2 F$ and $C Cl_3-CF_3$ which are commercially available as Freon -113.

The liquid is heated by means of a PTC resistor 15 which is connected to a suitably proportioned voltage source via its connections 17 and 18 which are fed out of the reservoir via suitable passages 21. PTC resistors (cold conductors) offer the advantage that a given temperature cannot be exceeded, because if the temperature increases, the resistance of the PTC resistor increases, so that the electrical power which is supplied by the voltage source and which is converted into heat in the PTC resistor decreases, thus counteracting a temperature rise. The PTC resistor and the voltage source must be matched so that a given temperature (for example, 330° K.) will definitely not be exceeded.

When the vapour pressure in the reservoir exceeds atmospheric pressure, vapour leaves the rigid reservoir 13 via the bore 12 and enters the cuff 9 in order to inflate the cuff until the temperature limit is reached, determined by the PTC resistor, and hence a given pressure is reached which must be higher than the systolic pressure to be expected. The cuff then blocks the finger artery. After disconnection of the voltage from the PTC resistor 15, the temperature of the liquid decreases, and hence also the vapour pressure, to an extent which is determined by the extent to which heat can be dissipated via the surrounding housing. Tests have demonstrated that it is sufficient when the lower portion 8 is made of metal (for example, brass). In that case a pressure decrease of approximately 6 mbar/s is obtained. The Korotkoff's sounds occurring during the pressure decrease are converted into electrical signals by means of a suitable, for example, piezoelectric converter 16 which is also arranged inside the reservoir, said signals being applied, via the connections 19 and 20, to a suitable evaluation circuit which is accommodated in the housing 7, like the voltage source for heating the PTC resistor, the circuit for pressure and temperature measurement as well as a control circuit.

Figure 4:
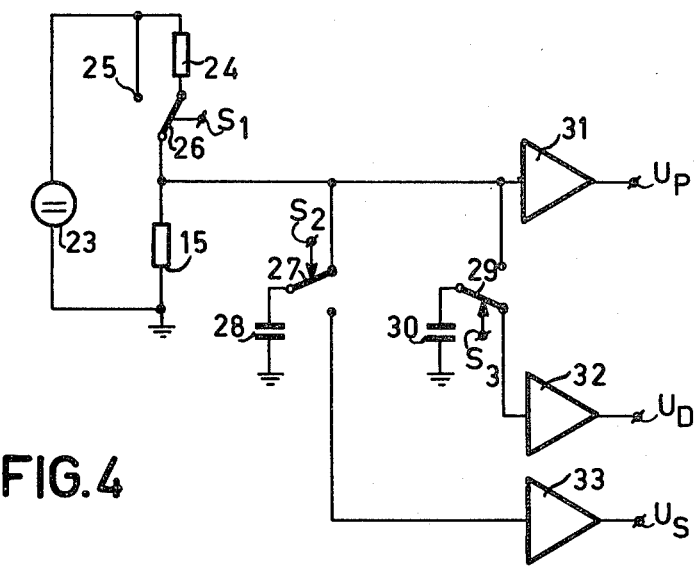
FIG. 4 shows a circuit in which a PTC resistor serves on the one hand as the heating element and on the other hand as the measuring element.

The circuit of operating the PTC resistor 15 as the heating element and the measuring element is shown in FIG. 4. During the first examination phase, the PTC resistor 15 is connected to a direct voltage source 23 by a switch 26 which is controlled preferably electronically via the control input $S_1$. The PTC resistor 15, and hence the liquid contained in the reservoir 13, is heated to a limit temperature which is dependent on the proportioning of the voltage source 23 and the temperature/resistance characteristic of the PTC resistor 15. After a period of time which is proportioned so that the liquid reaches the limit temperature even in worst case conditions, a pulse on the control input S switches the switch 26 over to the position shown in the drawing in which it is connected to the voltage source 23 in series with a resistor 24. The series resistor 24 is proportioned so that even at the limit temperature, it is large in comparison with the resistance of the PTC resistor 15, so that an essentially constant measuring current (which is much smaller than the current flowing through the PTC resistor in the heating phase) flows through the PTC resistor. The voltage across the PTC resistor is then a measure for its resistance, which in its turn is a measure for the relevant temperature in the liquid which, at least in the case of a vapour pressure in excess of the atmospheric pressure, is unambiguously related to the pressure in the cuff, i.e. the voltage across the PTC resistor 15 is a measure for the cuff pressure. This voltage is amplified by an amplified 31.

Instead of allowing the heating element to heat the liquid for a predetermined period of time, it is alternatively possible to heat only until a predetermined temperature, so a predetermined vapour pressure is reached. To this end, during the heating operation the temperature (pressure) should be measured at short time intervals, for example, by briefly switching over the switch 26. The measurement, however, can alternatively be realized by means of a separate temperature sensor, for example, an NTC resistor. This would also preclude overheating of the PTC resistor, which could occur in the case of inexpert use (impermissible thermal insulation of the housing) because the temperature is exceeded beyond which the PTC resistance decreases again as the temperature increases.

In the simplest case, the output voltage $U_p$ of the amplifier 31 could be applied, for example, to a moving coil instrument whose scale is calibrated in units of pressure, so that this scale serves somewhat like a memory for the pressure occurring at the relevant temperature of the liquid used.

For the diagnosis, the difference between the cuff pressure and the atmospheric pressure is important rather then the pressure inside the cuff. Because the atmospheric pressure is not always constant, errors may occur during the evaluation. If these errors are not to be tolerated, they can be eliminated by subtraction of the atmospheric pressure. The atmospheric pressure can be defined, for example, before or after the measurement, as the cuff pressure at which the cuff is just inflated or collapses again. For the described example with a moving coil instrument, this correction can be performed by mechanically setting the pointer of the moving coil instrument to zero at the relevant pressure. Obviously, electrical subtraction is alternatively possible.

The systolic and the diastolic blood pressure are determined by means of a further amplifier 33 and 32, respectively, as well as a capacitor 28 and 30, respectively, one terminal of which is connected to ground while the other terminal can be connected, by means of a switch 27, 29, respectively, to the PTC resistor 15, i.e. to the input of the amplifier 31, or to the input of the amplifier 33 or 32, respectively. The switch 27 or 29 is electronically controlled on the terminal $S_2$, $S_3$, respectively, which receives the pulses from the circuit which evaluates the Korotkoff's sounds. When the systolic blood pressure is reached, a pulse on the terminal $S_2$ connects the capacitor connection to the input of the amplifier 33, the impedance of the input of which is so high so that the capacitor can only be gradually discharged.

Figure 5:
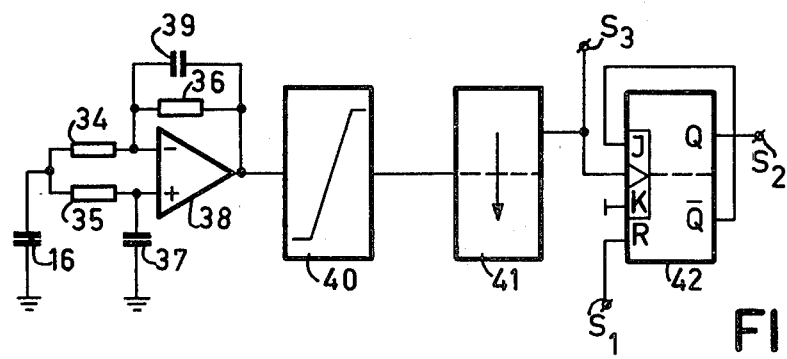
FIG. 5 shows a circuit for determining Korotkoff's sounds.

The circuit for evaluating the Korotkoff's sounds is shown in FIG. 5. The electrical signals which correspond to the pressure variations are applied from the piezoelectric detector 16, being represented by a capacitance in the circuit diagram, to an amplifier 38 which is designed as a band-pass filter for signals in the frequency range of the Korotkoff's sounds. The lower cut-off frequency is determined by the RC element 35, 37 and the upper cut-off frequency is determined by the RC element 36, 39. Via a Schmitt trigger 40 and a monostable multivibrator 41, a pulse is produced for each heart beat when Korotkoff's sounds occur, said pulse being available on the terminal $S_3$ which forms inter alia the control input for the switch 29. Thus, this switch is continuously switched to and fro until it remains in the position shown when the level of the Korotkoff's sounds has become so low when the diastolic blood pressure value is reached that the Schmitt trigger 40 is no longer activated.

The output of the monostable multivibrator 41 has connected to it a JK flipflop 42 which produces a pulse on its output $S_2$, which inter alia also controls the switch 27, only when the first pulse appears on the terminal $S_3$, and which can be reset by a pulse on its terminal $S_1$ which is connected to the reset input R and whose potential also controls the switch 26.

Figure 6:
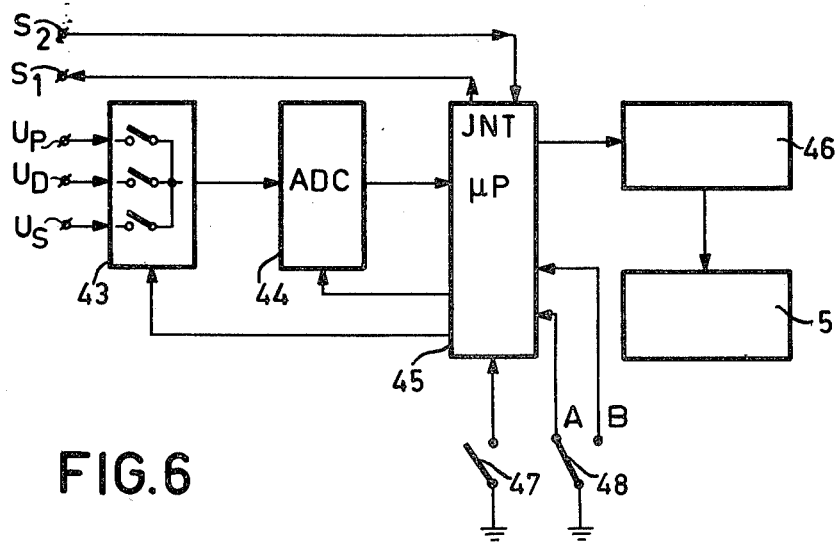
FIG. 6 shows a control circuit which includes a microprocessor.

FIG. 6 shows a control circuit for controlling the circuits shown in the FIGS. 4 and 5 and for processing the measurement values produced by these circuits. The central component of this circuit is formed by a microprocessor 45. The output voltages of the amplifiers 31, 32 and 33 which correspond to the pressure are first applied to an analog switch 43 which is controlled by the microprocessor and which is followed by an analog-to-digital converter 44 which converts its analog input signal into a digital output signal which is applied to the microprocessor. Via a decoder 46, the microprocessor 45 controls a display unit 5. A start key 47 produces a start signal which initiates the control by the microprocessor 45, and a switch 48 determines which of the two blood pressure values is output (for example, in the position A the systolic blood pressure, and the diastolic blood pressure in the position B).

After activation of the start key, all memories for the measurement variables in the processor are set to zero. At the same time, on signal $S_1$ a signal is output which switches the switch 26 to the contact 25 ("heating") and which resets the flipflop 42. After approximately 10 seconds, i.e. a period of time within which the liquid has been heated to a sufficiently high temperature, a further pulse switches over the switch 26 to the position shown in FIG. 4. The subsequent part of the program can be interrupted any time by a pulse on the interrupt input of the microprocessor which is connected to the terminal $S_2$. As has already been stated, this pulse is generated when the difference between the cuff pressure and the atmospheric pressure corresponds to the systolic blood pressure value. The voltage $U_{syst}$ on the output of the amplifier 33, therefore, is a measure for the systolic blood pressure at the given atmospheric pressure. The microprocessor 45 switches the analog switch 43 to the output of the amplifier 33 which converts the signal, via the analog-to-digital converter 44, into a digital signal which is stored in a memory of the microprocessor. From a table which is stored in a read-only memory and in which different pressures are associated with different voltages, the pressure associated with the measurement value $U_{syst}$ is interpolated.

Subsequently, the analog switch 43 is connected to the output of the amplifier 31 and the voltage $U_P$ produced is compared with a value which is smaller than the diastolic blood pressure value to be normally expected. For as long as the pressure has not yet decreased so far, the instantaneous value $U_P$ is continuously written in and compared again. The pulses produced at the rhythm of the heart beat on the terminal $S_3$ each time switch over the switch 29 until the Korotkoff's sounds disappear, after which a voltage $U_{diast}$ which corresponds to the diastolic pressure is present on the output of the amplifier 32. When the cuff pressure has dropped below said lower threshold value, this part of the program is terminated, and subsequently the analog switch 32 is connected to the output of the amplifier 32, the output voltage of which is converted into a digital value which is stored in a memory of the microprocessor. This value is again associated with a pressure value. After subtraction of a value corresponding to the possibly previously measured atmospheric pressure, the two values are displayed.

Figure 3:
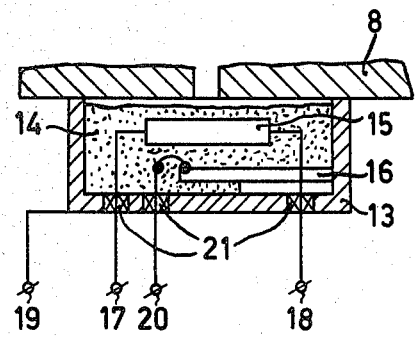
FIG. 3 shows the reservoir with the heating element and a converter element.

The embodiment shown in the FIGS. 1 to 3 utilizes a semicircular finger cuff, for example, as known from DE-OS No. 28 42 337. However, a cuff which completely encloses the finger during measurement, for example, as known from DE-OS No. 18 17 089, can also be used.

It is not necessary to determine the pressure in the cuff by way of temperature measurement. Direct measurement is also possible, for example, by means of a piezoresistive element whose resistance changes in dependence of the pressure acting thereon. Not only the quasi-static pressure in the cuff can be measured thereby, but also the pressure variations in the cuff which are caused by the Korotkoff's sounds (the signals caused by the pressure variations must in this case be separated by way of a suitable high-pass filter). If the liquid is not heated, the pressure in the cuff assumes a value which corresponds to the relevant atmospheric pressure. This pressure can be determined by means of the piezoresistive element and be subtracted from the subsequently determined values $U_{sust}$ and $U_{syst}$.

What is claimed is:
1. A blood pressure measuring device comprising:
cuff means which function to apply pressure to a body part;
fluid reservoir means which communicate with the interior of the cuff;
a liquid having a boiling point between 290° K. and 340° K. disposed in the reservoir means;
means for measuring pressure in the cuff;

electric heating means disposed in the liquid which function to heat the liquid above its boiling point to increase vapor pressure in the cuff.

2. A blood pressure measuring device as claimed in claim 1, characterized in that the liquid comprises diethylether.

3. A blood pressure measuring device as claimed in claim 1, characterized in that the liquid comprises acetone.

4. A blood pressure measuring device as claimed in claim 1, characterized in that the liquid comprises a fluorinated hydrocarbon.

5. A blood pressure measuring device as claimed in claim 1, characterized in that the heating means comprises a PTC resistor.

6. A blood pressure measuring device as claimed in claim 1, characterized in that the means for measuring the pressure in the cuff comprises a temperature sensor for measuring the temperature of the liquid, a memory means for storing the temperature/vapour pressure characteristic of the liquid, and means for determining the vapour pressure associated with said liquid temperature from said stored temperature/vapour pressure characteristic.

7. A blood pressure measuring device as claimed in claim 6, characterized in that the temperature sensor comprises a PTC resistor.

8. A blood pressure measuring device as claimed in claim 1, further comprising a piezo-resistive element disposed in the liquid to detect the pressure variations caused by Korotkoff sounds.

* * * * *